United States Patent [19]
Korth

[11] Patent Number: 5,480,881
[45] Date of Patent: Jan. 2, 1996

[54] TREATMENT OF DISEASE WITH PAF-ACETHER ANTAGONISTS AND PROCEDURE DETERMINING THEIR EFFICACY

[76] Inventor: Ruth Korth, Palestrinastr. 9, D-8000 Munchen 19, Germany

[21] Appl. No.: 104,599

[22] Filed: Aug. 11, 1993

Related U.S. Application Data

[63] Continuation of Ser. No. 844,882, Mar. 3, 1992, abandoned, which is a continuation-in-part of Ser. No. 704,554, May 23, 1991, abandoned.

[30] Foreign Application Priority Data

Jun. 1, 1990 [DE] Germany ............................ 40 17 818.8
Oct. 26, 1990 [DE] Germany ............................ 40 34 090.2

[51] Int. Cl.⁶ ..................................................... A61K 31/55
[52] U.S. Cl. ............................................ 514/220; 514/219
[58] Field of Search ...................................... 514/219, 220

[56] References Cited

U.S. PATENT DOCUMENTS

| | | | |
|---|---|---|---|
| 4,582,824 | 4/1986 | Nishikawa et al. | 514/77 |
| 4,761,404 | 8/1988 | Bugianesi et al. | 514/77 |
| 4,900,729 | 2/1990 | Stransky et al. | 514/220 |
| 4,914,096 | 3/1990 | Houlihan et al. | 514/220 |
| 5,028,603 | 7/1991 | Tahara | 514/220 |

*Primary Examiner*—Kimberly R. Jordan
*Attorney, Agent, or Firm*—Nikaido, Marmelstein, Murray & Oram

[57] ABSTRACT

The present invention is directed to the treatment of a disease caused by an amount of pathogenic LA-paf in lipoproteins and cells comprising administering to a subject requiring the treatment an effective amount of a paf-acether antagonist.

1 Claim, 9 Drawing Sheets

TREATMENT OF DISEASE WITH PAF-ACETHER ANTAGONISTS AND PROCEDURE DETERMINING THEIR EFFICACY

This application is a continuation of application Ser. No. 07/844,882, filed on Mar. 3, 1992, now abandoned which is a continuation-in-part of application Ser. No. 07/704,554, filed May 23, 1991, now abandoned.

The invention refers to the treatment of diseases with paf-acether antagonists and a procedure for determining their efficacy.

According to its chemical structure paf-acether (paf, platelet-activating factor) is 1-0-alkyl-2-acetyl-sn-glyceryl-3-phosphocholine in C. R. Acad. Sci., Paris, No. 289, 1979, p. 1037–1040.

It is known that paf-acether induces the aggregation of platelets in J. Exp. Med. 136, 1972, p. 1356–1377. Accordingly, it has been proposed to treat diseases caused by paf-acether mediated platelet activation with natural occuring Ginkgolides in Eur. J. Pharmacol., 1988, 152, p. 101–110. Ginkgolides are paf-acether antagonists, that means compounds which inhibit the paf-acether binding sites for platelets so that the se cells are not attacked by paf-acether in U.S. patent application Ser. No. 07/259,674.

It has now been discovered that the platelet activation is not only induced by a paf-acether, but also by lipoproteins (normal or modified), particularly LDL (low density lipoproteins), and by lipoprotein-associated paf (LA-paf).

In addition, it has been discovered that the platelet activation induced by lipoproteins (normal and modified) and LA-paf i s inhibited by paf-acether antagonists.

That means, paf-acether antagonists can be used to treat a disease caused by lipoproteins (normal or modified) or LA-paf.

As paf-acether antagonist a hydrophilic or non-hydrophilic triazolothieno-diazepine or an analogue thereof, a Ginkgolide, a Ginkgolide mixture or a synthetic Ginkgolide derivative, or an analogue of paf-acether, as CV 3988, can be used according to the invention. The triazolothienodiazepine is preferably WEB 2086, WEB 2098 or BN 50739 and the Ginkgolides are preferably BN 52020, BN 52021 or BN 52022 or mixtures with/of these compounds.

The chemical formula of BN 50739 is tetrahydro-4,7,8,10 methyl(chloro-2 phenyl) 6[dimethoxy-3,4-phenyl)thio] methylthiocarbonyl-9 pyrido [4',3'-4,5 ]thieno [3,2-f]triazolo-1,2,4 [4,3-a]diazepine-1,4).

The chemical term of CV 3988 is rac-3-(N-n-octadecyl carbamoyl oxy)-2-methoxypropyl 2-thiazolioethyl phosphate; the term of WEB 2086 is 3-(4-(2-chlorophenyl)-9-methyl-6H-thieno(3,2-f) (1,2,4) triazolo-(4,3-a)-(1,4) diazepine-2yl)-1-(4-morpholinyl)-1-propanone;the term of WEB 2098 is (3-(4-(2-chlorophenyl)-9-cyclopropyl-6H-thieno (3,2-f)- (1,2,4) triazolo-(4,3-a) (1,4) diazepine-2yl)-1-(4-morpholinyl)-1-propanone;the term of BN 52020 is 9H-1,7a-(Epoxymethano)-1H, 6aH-cyclopenta [c]furo [2,3-b]furo [3',2':3,4]cyclopenta [1,2-d]furan-5,9,12-(4H)-trione, 3-tert -butylhexahydro-4,7b-dihydroxy-8-methyl; the term of BN 52021 is 9H-1,7a-(Epoxymethano)-1H,6aH-cyclopenta[c]furo [2,3-b]furo-[3',2':3 4]cyclopenta[2-d]furan-5,9,12(4H)-trione, 3-tert-butylhexahydro-4,4b-11-trihydroxy-8-methyl; and the term of BN 52022 is 9H-1,7a-(Epoxymethano)-1H, 6aH-cyclopenta[c]furo3',2':3,4] cyclopenta [1,2 -d]furan-5,9,12(4H)-trione, 3-tert-butylhexahydro-2,4,7b,11-tetrahydro- 8-methyl.

It is known to determine the efficacy of paf-acether antagonists by competitive binding tests. However, a reliable information about the efficacy of paf-acether antagonists is only possible in case the incubation of the cells and the labelled paf-acether is performed in the presence and in the absence of lipoproteins (normal or modified), particularly LDL or VLDL (very low density lipoprotein).

In order to conduct a quick and simple test on the effect of the substances with regard to their antagonistic activity vis à vis paf-acether receptors, i.e, to use a screening procedure, for example, to find effective antagonists to paf-acether receptors, which can then be taken into consideration for treating the disease mentioned, then according to the invention, the best method is to proceed as follows:

a) a given quantity of purified cells is mixed with a given quantity of labelled paf-acether and the antagonist to be determined in the presence of lipoproteins (normal or modified) and/or cholesterol, or LA-paf, b) a given quantity of the same purified cells is mixed with a given quantity of labelled paf-acether in the presence of lipoproteins (normal or modified) and/or cholesterol, or LA-paf, c) the cells are separated from the mixtures a) and b) in each case, d) the quantity of labelled paf-acether bound to the cells is measured in each case, and e) the efficacy of the paf-acether antagonist is determined from the relationship between the quantity of labelled paf-acether which is bound to the cells according to a) in the presence of the antagonist on one hand, and the quantity of labelled paf-acether which is bound to the cells according to b) in the absence of the antagonist on the other hand.

Preferably, platelets are used as cells for the procedure of the invention for determining the efficacy of paf-acether antagonists.

Preferably, the cells are subjected to a treatment in which the cells are purified, for instance by washing or gel filtration, and preferably aspirin is added. The addition of aspirin eliminates adverse effects of prostaglandins on the procedure for determining the efficacy of paf-acether antagonists according to the invention. Additive effects of aspirin and prostaglandine-antagonists could also be determined.

In case of platelets, thereafter the purified cells are preferably dispersed in a isotonic buffer containing delipidated serum albumin, but no calcium ions. In case platelets are used, they are concentrated several times, for instance ten times, before they are used in steps a) and b) in the procedure according to claim 7 in the presence of calcium and magnesium ions.

As labelled ligand tritium-labelled paf-acether or labelled antagonists such as labelled WEB 2086 can be used, for instance. It is also possible to use labelled or unlabelled paf analogues as well as coloured or fluorescence labelled compounds.

The mixing according to the steps a) and b) of claim 7 is done preferably at a temperature of 20° C. After mixing, the cells are incubated preferably more than 10 min. before they are separated according to the step c) of the procedure of the present invention. The incubation period is preferably more than 10 min. The separation of the cells according to step c) can be performed by filtration or centrifugation.

Besides platelets monocyte-macrophage-like cells can be used in the procedure for determining the efficacy of paf-acether antagonists according to the present invention.

In this case, monocyte-macrophage-like cells are used, which are stimulated with lipoproteins (normal or modified) and/or cholesterol in a delipidated medium.

When monocyte-macrophage-like cells are used, the procedure of the present invention is particularly quick and simple. Monocyte-macrophage-like cells are commercially available and can be cultivated without problems. Only a certain quantity of cells has to be taken from the culture which are stimulated with cholesterol or a lipoprotein, as LDL or VLDL, before the binding studies. These operations and the binding study itself can be conducted with operations which are standard operations in a laboratory, so that commercial automatic devices can be used. Accordingly, the procedure of the present invention can be conducted automatically, what is of great importance for a screening procedure.

In case monocyte-macrophage-like cells are used, the procedure of the present invention can also be used for determining the activity of a paf-acether antagonist for the prophylaxis and treatment of arteriosclerosis. In the pathogenesis of arteriosclerosis but also inflammatory diseases or cancer, monocyte-macrophage-like cells and lipoproteins (normal or modified), as LDL, and cholesterol contained therein, have a considerable importance.

Accordingly, in the procedure of the present invention, similar cells are used in vitro together with LDL and cholesterol, which cause arteriosclerosis in vivo.

As monocyte-macrophage-like cells U 937 cells are particularly preferred.

The cultivation of the monocyte-macrophage-like cells is performed in a culture medium which contains a serum, particularly fetal calf serum. Before the test, the monocyte-macrophage-like cells are incubated preferably in a medium containing delipidated serum, particularly delipidated fetal calf serum for several hours. LDL and cholesterol are added preferably 24 h after starting the incubation, to stimulate the cells. The culture medium for the monocyte-macrophage-like cells contains preferably L-glutamin. The cultivation and incubation, respectively, is conducted at an elevated temperature of for instance 37° C.

Besides the simple cultivation monocyte-macrophage-like cells have the essential advantage that they are present in a suspension so that they can be dispensed in a exact quantity with conventional commercial devices.

Before the cells are used for the binding studies, they have to be purified for instance by washing to remove enzymes as acetylhydrolase decomposing paf-acether.

In case of monocytic macrophage cells the binding studies are conducted at a temperature of less than 20° C., preferably between 2 and 6° C., to avoid a decomposition of paf-acether by the enzymes contained in the monocyte-macrophage-like cells as phospholipase or acetylhydrolase. After mixing according to the steps a) and b) of the procedure of the present invention, an incubation of preferably between 10 min. and 1 to 4 h is performed in case monocyte-macrophage-like cells are used.

Since paf-acether is a phospholipid which does not dissolve readily in water, the binding studies are preferably performed in the presence of delipidated serum albumin, as bovine serum albumin, and preferably calcium and magnesium ions are added.

The task of the serum albumin is to bind paf-acether and the antagonist which is not specifically bound to the monocyte-macrophage-like cells, so that this part of paf-acether and antagonist, respectively, is removed from the monocyte-macro-phage-like cells.

In order to separate the monocyte-macrophage-like cells treated in this way from the liquid medium, it is preferable to filter them, because they are very easy to filter. At the same time, filtering constitutes a relatively precise and therefore very effective procedure for separating from the cells the remaining labelled paf-acether which is unspecifically bound.

After this, the quantity of labelled paf-acether which is (specifically) bound to the cells is determined. If radioactively labelled paf-acether is used, only the radioactivity of the cells bound in the filter is measured. The radioactivity bound in the filter where there are no cells is substracted from these values.

By drawing calibration graphes, which are obtained with varying quantities of the antagonist in accordance with step a), it is thus possible to obtain the efficacy of the antagonist at a 50% inhibitory value, i.e. as that quantity of the antagonist which, in relation to a given quantity of cells, leads to a 50% inhibition of the reversible paf-acether binding.

The procedure of the present invention in which monocyte-macro-phage-like cells are used has been tested successfully particularly with WEB 2086 as hydrophilic triazolothieno-diazepine.

In addition, the procedure of the present invention can be used to determine the efficacy of a particular compound as to its activity vis à vis acetylhydrolase, which is a natural antagonist of paf-acether. Furthermore, LDL and cholesterol stimulate the intracellular formation of acetylhydrolase, and the procedure of the present invention can be used for the formation of acetylhydrolase and its antibodies. In addition, with the procedure of the present invention the pathogenity and atherogenity, respectively, of LDL preparations of patients, preferably hypercholesterolemics, can be tested clinically and can be correlated with their amount of LA-paf in pathogenetic lipoproteins such as apolipoprotein (a) or apolipoprotein B (100).

Furthermore, besides cholesterol the effects of other steroids, as corticosteroids or sexual hormons can be tested in screening procedure according to the present invention.

In addition, binding sites for paf or LA-paf, receptor modulating proteins and binding sites for paf antagonists as for instance WEB 2086, can be formed using differentiated cell lines such as LDL and/or cholesterol treated monocyte-macrophage-like cells. With these systems monoclonal antibodies can be synthesized which can be used in the treatment or diagnosis of various diseases. Monoclonal antibodies against the protein portion in paf like compounds such as LA-paf can also be formed for diagnostic tests. Since LA-paf was formed in monocyte-macrophage-like cells (as well as in platelets together with lipoproteins), these cells can be used to synthesize LA-paf or labelled LA-paf.

The increased binding of paf or paf-like compounds on the surface of platelets can be used for a simple quantitation of these substances as proposed in German patent application P 37 35 524.4. The cell-bound paf or paf-like compounds such as LA-paf can be measured in their potency to mediate cell adherence, platelet aggregation or various substrate reactions including their reactions with coloured or fluorescence antibodies. Blood cells such as platelets can be easily isolated without phospholipid extraction and HPLC-analysis by filtration or centrifugation methods. For a filtration procedure sticks with automatic devices are commercial available. Finally paf receptors are stable for five days and thus the receptor status of blood cells can be investigated in central institutes when blood is taken into special testing containers which are commercial available and which should be modified for smaller blood volumes as proposed in German utility model application G 87 16 004.8.

Since the specific binding of paf or paf-like compounds such as LA-paf is in close correlation with the cellular calcium stream, the procedure of the present invention can also be used for measuring paf-acether or paf-like blood components, by comparing their effect on the cellular calcium stream with calibration graph of synthetic paf-acether. For an automatization of calcium measurements commercial automatic devices are available.

The compounds of the present invention, which block lipoprotein and lipoprotein-associated PAF-acether receptor sites on platelets and thus substantially inhibit platelet aggregation or activity are effective in treating diseases associated with lipoprotein or lipoprotein-associated PAF-acether mediated platelet activation, including but not limited to the treatment of arteriosclerosis, inflammatory diseases, cancer, hyperlipidemia and the like.

The inhibitory binding agent of this invention may be administered to warm-blooded animals topically, orally, parenterally, transdermally or by inhalation. The agents are present as the active ingredients in conventional pharmaceutical preparations, e.g. in compositions consisting essentially of an inert pharmaceutical carrier and an effect dose of the agent, such as tablets, both plain and coated, capsules, lozenges, powders, solutions, suspensions, aerosols for inhalation, ointments, emulsions, syrups, suppositories, etc. An effective dosage of the agents according to the invention is between 1 and 50 mg, preferably between 3 and 20 mg per does for oral administration, and between 0.01 and 50 mg, preferably between 0.1 and 10 mg per dose for intravenous or intramuscular administration. For inhalation, solutions should be used containing 0.01 to 1.0, preferably 0.01 to 0.5% of the agent. The following examples serve to explain the invention more clearly:

1. Lipoprotein isolation

Figure 1:
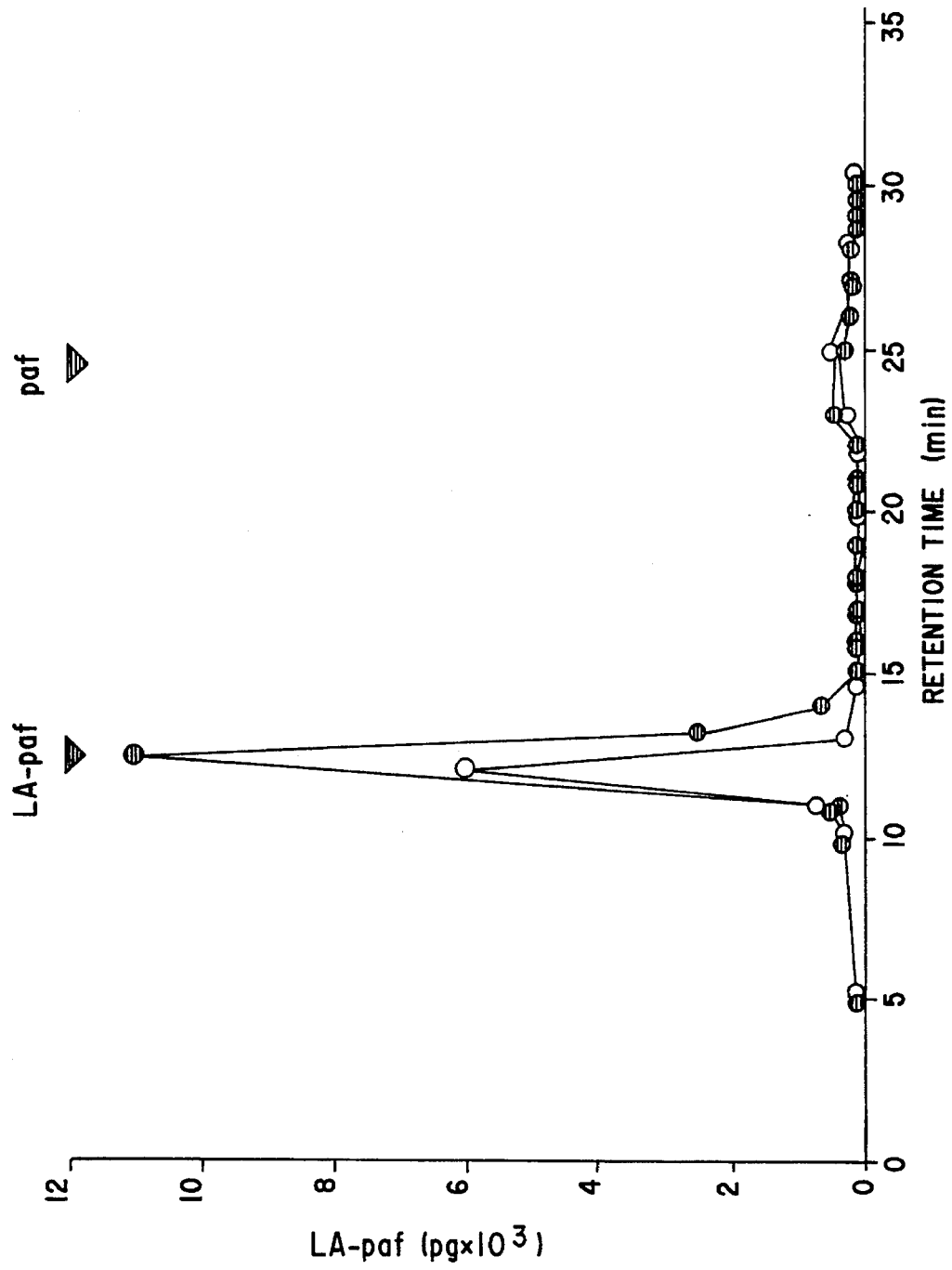
FIG. 1 shows the presence of LA-paf in human lipoproteins and differences between LA-paf and synthetic paf using high pressure liquid chromatography.

LDL was obtained as described in J. Clin. Invest., 955, No. 34, p. 1345–1353, that means by ultracentrifugation and dialysis against 0.15M NaCl/1 mM EDTA, pH 7.5. The lipoprotein-fraction was stored at 4° C. and used within 1 week.

2. Preparation of washed platelets and platelet aggregation

According to Br. J. Haematol., 1983, No. 53, p. 513, modified in accordance with Eur. J. Pharmacol., 1988, No. 152, p. 101–110, platelets were obtained from healthy male volunteers. The human blood was taken from the cubital vein in ACD (Acid Citrate Dextrose) 7:1 and centrifuged (100×g, 5 min.) to obtain a platelet-rich plasma. The platelets were then washed three times by centrifugation (900×g, 10 min.) in Tyrode's buffer containing ACD 9:1 (pH 6,4) and incubated with lysin-aspirin (100μM) for 30 min. prior to the last wash. The final platelet concentration was adjusted to 1×10$^8$ platelets per ml by use of a Coulter Counter. After the last wash they were suspended in the pH 6,4 Tyrode's buffer containing 0.25 % BSA (Fatty Acid Bovine Serum Albumin BSA) without ACD and Ca$^{2+}$(10$^9$ platelets per ml) to be diluted directly before the binding experiment with a pH 7.4 Tyrode's buffer containing 0.25 % BSA and 1.3 mM Ca$^{2+}$. Platelet aggregation was performed as described in Br. J. Haematol., 1983, No. 53, p. 513 with synthetic paf (50 nM), LA-paf or thrombin (1 U) under stirring at 37° C. in the presence of human fibrinogen with or without different concentration of WEB 2086.

3. Isolation of LA-paf from lipoproteins, platelets and monocyte-macrophage-like U 937 cells A phospholipid extraction was performed using the method described in Can. J. Biochem. Physiol., 1959, No. 37, p. 911–917, modified according to Eur. J. Pharmacol., 1988, No. 152, p.101–110. The phospholipids were extracted from lipoproteins or sonicated platelets as well as monocyte-macrophage-like U 937 cells cultured in standard 10% fetal calf serum (FCS) containing RPMI medium). Dichloromethane/methanol (½, v/v) was added over night at 4° C. before adding dichloromethane/water (1/1, v/v.) containing 2% acetic acid. The organic phases were collected and the water phases were washed three times with 1 volume dichloromethane. The samples were applied to a high pressure liquid chromatography (hplc) Microporsil column (3.9 mm ID×300 mm length) which was then diluted to a flow rate of 1 ml/min. as described in C. R. Acad. Sci. (Paris), No. 289, p. 1037–1040, 1979. LA-paf was identified by comparison to radioactive standards of phosphocholine (PC), sphingomyelin, synthetic paf and lysophosphatidyl-choline. The phospholipids were stored at 4° C. after evaporation of dichloromethane and quantified within one week using aggregation of asparinated and CP, CPK (Creatinphosphate/Creatinphosphokinase)-treated rabbit platelets (3×10$^8$ platelets per ml) according to J. Exp. Med., 1972, No. 136, p. 1356–1377, with a slight modification since rabbit platelets were washed as described above for human platelets. Lysin aspirin (100μM) was incubated for 30 min. prior to the last wash of the platelets. CP (1 mM) and CPK (10 U per ml) were added directly before aggregation measurements. The aggregatory activity of LA-paf was expressed as ng paf equivalent activity as compared with standards of synthetic paf and calculated in nM on the basis of the molecular weight of synthetic paf. The inhibitory WEB 2086 effect on paf-mediated platelet aggregation was tested using a concentration of LA-paf or synthetic paf which mediates 80% (EC$_{80}$) of the maximal light transmission after 1 min. pre-incubation at 37° C. with different concentrations of WEB 2086. The IC$_{50}$-values were then calculated as 50% inhibitory WEB 2086 concentrations from the graphics.

4. $^3$H-paf binding studies to washed human platelets paf binding studies were performed by addition of labelled (0.065 or 0.65 nM with 26.1 nCi, Amersham Bucks U.K.) and unlabelled synthetic paf (0.01–50 nM) or WEB 2086(1μM) to the BSA-containing buffer (0.25%, w/v) prior to the addition to the platelets (see Thrombos. Res., 1986, No. 41, p. 699–706). LDL (20 μg per 500 μl, final concentrations), LA-paf (1 nM), unlabelled synthetic paf (1 nM) or vehicles were also added to the cell free buffer prior to the addition of the platelets. Binding experiments were then started by addition of 50 μl platelet suspension to 400 μl buffer after addition of 50 μl labelled paf. The platelets were separated from the supernatants after 30 min. incubation at 20° C. using vacuum filtration.

For the desensitization studies LA-paf, synthetic paf (10 nM) or LDL (85 μg per 500 μl) were incubated with platelets 3 min. before the addition of labelled and/or unlabelled synthetic paf. In these experiments, platelets ($10^9$ per ml) were treated with 2.5 mg antibodies against human lipoproteins or human serum albumin or vehicle (40 min. at 20° C.) prior to the last wash. The labelled paf binding was calculated as fmol bound to $5\times10^7$ platelets or expressed as percent of the specific $^3$H-paf binding verified with unlabelled synthetic paf (50 nM) or WEB 2086 (1μM). The values are means ±1 s.d. from three different experiments.

FIG. 1 shows the presence of LA-paf in human lipoproteins. The LA-paf from LDL obtained from two healthy male volunteers (● ○) coeluted in the HPLC-fractions (at 11–15 min.) with the functionally inactive phosphocholine. This retention time was clearly different from that of synthetic paf (at 21–24 min.) (FIG. 1). Calculating the activity of LA-paf in the LDL fractions from its ability to stimulate platelet aggregation in comparison of paf standards, 4.6±1.3 ng LA-paf per mg lipoprotein was formed with respect to VLDL 3.4±0.6 ng per mg and to HDL 2.5±1.3 ng per mg lipoprotein was measured, as compared with 0.2±0.2 ng per mg protein in lipoprotein poor serum from three healthy male volunteers (mean ± s.d.).

When extracting washed platelets from normal male volunteers $10^9$ platelets contained 3.1±0.5 ng LA-paf (data not shown).

It was partly released during aggregation of washed human platelets (n=3) in response to exogenous pal (50 nM) or thrombin (1 U). The LA-paf concentration of washed platelets was decreased to 2.2±0.2 and 2.1±0.1 ng per $10^9$ platelets after 1 min. aggregation indicating the cellular origin of LA-paf. The presence of LDL in these washed human platelets was verified qualitatively using SDS gel electrophoresis as described in J. Lipid Res., 1980, 19, p. 693–700. Platelets remained intact during aggregation, since no LDH release was detected (6.5±1.5%, means ±1 s.d., n=3). As compared with platelets washed monocyte-macrophage-like U 937 cells contained 133 ng per $10^9$ cells.

Figure 2:
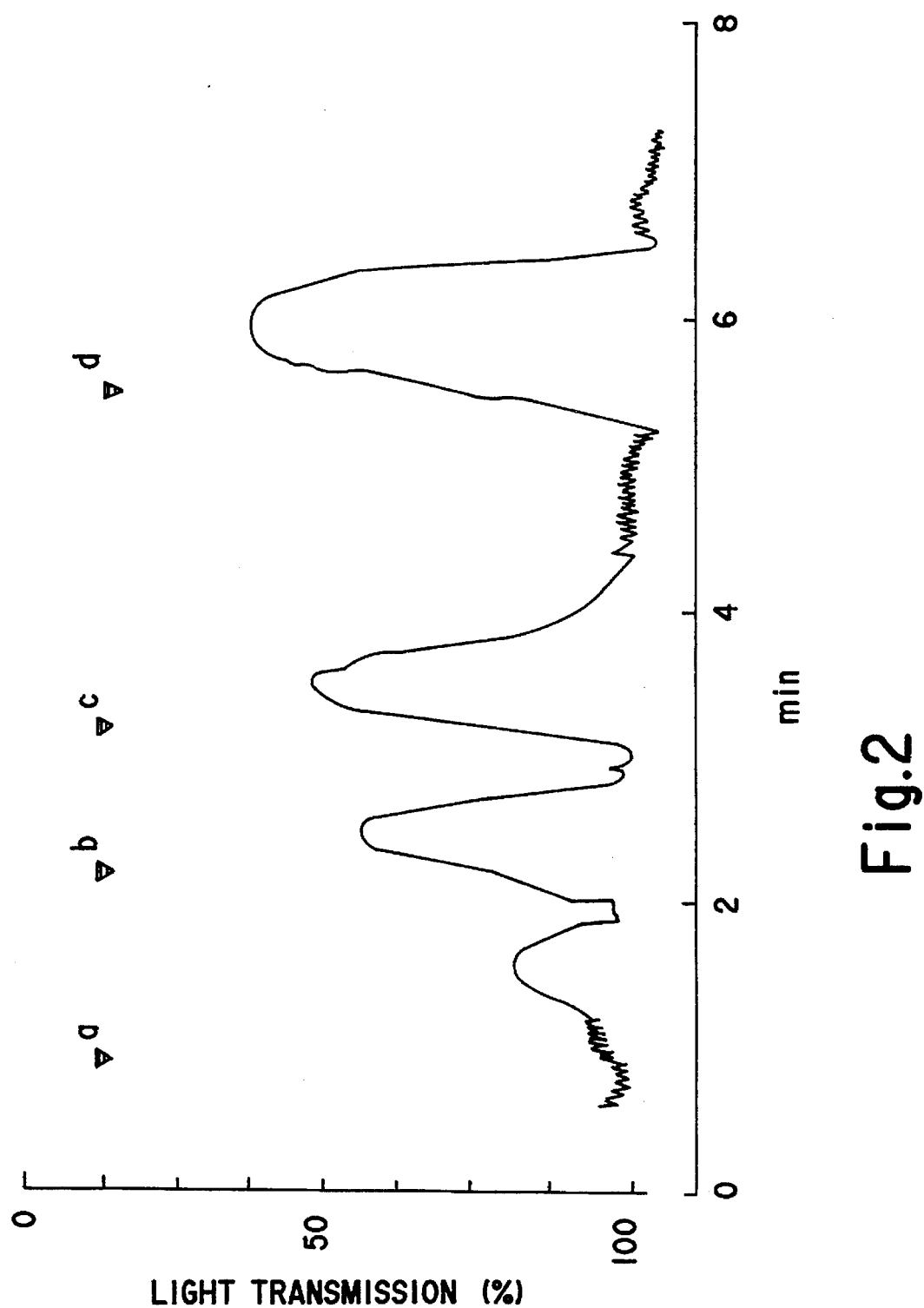
FIG. 2 shows a dose response curve of rabbit platelet aggregation with LA-paf.

FIG. 2 shows a dose response curve of rabbit platelet aggregation in response to LA-paf. Different concentrations of LA-paf (a: 32 pM, b: 68 pM, c: 83 pM, d: 109 pM, final concentrations) fractionized before using HPLC were added to the platelets under stirring as compared with defined standards of synthetic paf. Each value is representative of three experiments. That means, according to FIG. 2 the platelet aggregation is measured in dependence of the concentration and the time so that areas for the enhanced light transmission (platelet aggregation) and therefore reproducable values are obtained. As can be seen, the light transmission and therefore the platelet aggregation increases with the concentration of LA-paf.

Figure 3:
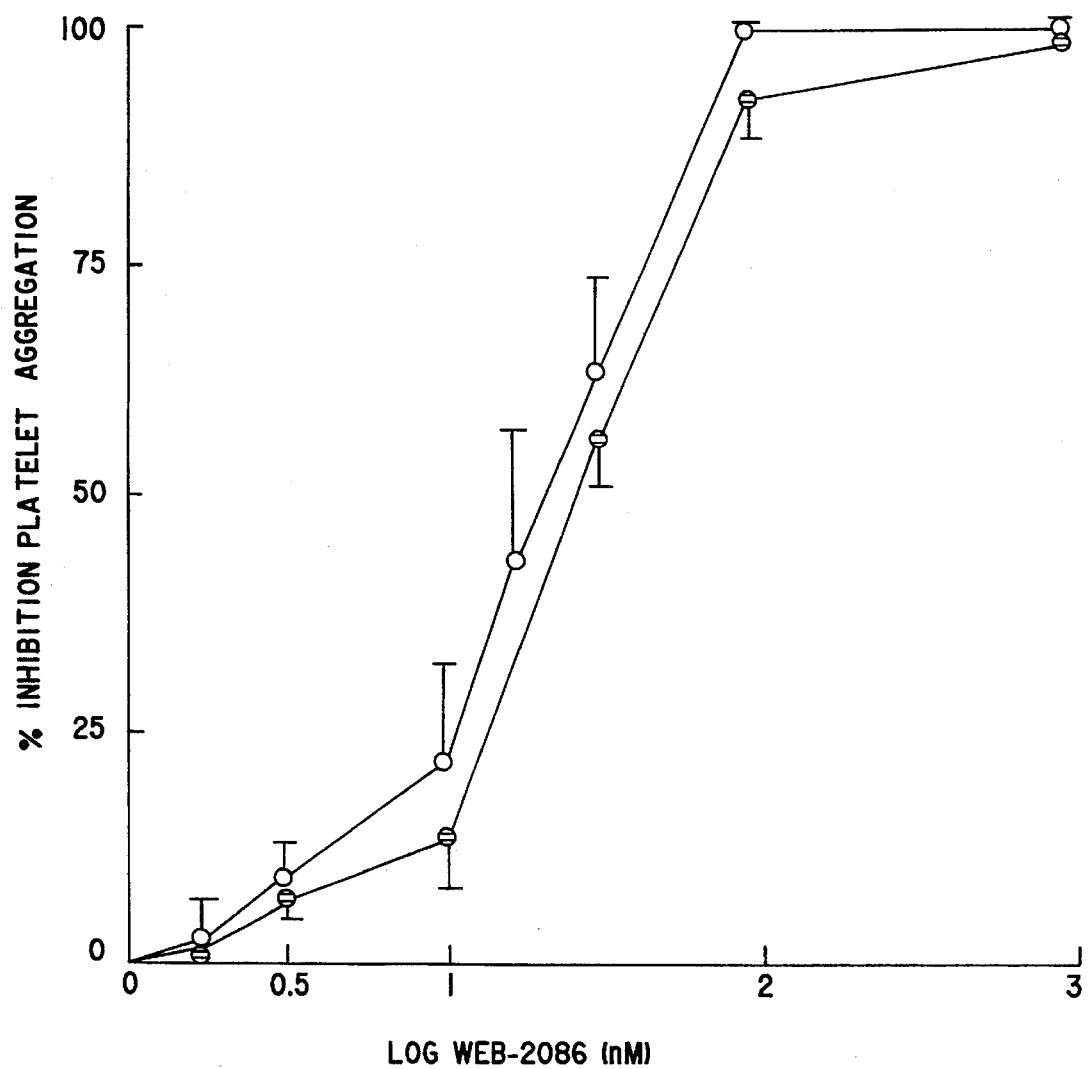
FIG. 3 shows the inhibition of rabbit platelet aggregation with LA-paf and synthetic paf in response to increasing concentrations of the triazolothieno-diazepine WEB 2086.

FIG. 3 shows the inhibition of rabbit platelet aggregation with LA-paf (○) and synthetic paf (●) after treatment with aspirin and CP/CPK in response to increasing concentrations of the antagonist WEB 2086. The values are means ±1 s.d. of three experiments. As can be seen, WEB 2086 as paf-acether antagonist shows practically the same effect vis à vis LA-paf and paf-acether. That means, WEB 2086 inhibits the platelet aggregation caused by LA-paf to the same extent as the platelet aggregation caused by paf-acether.

Figure 4:
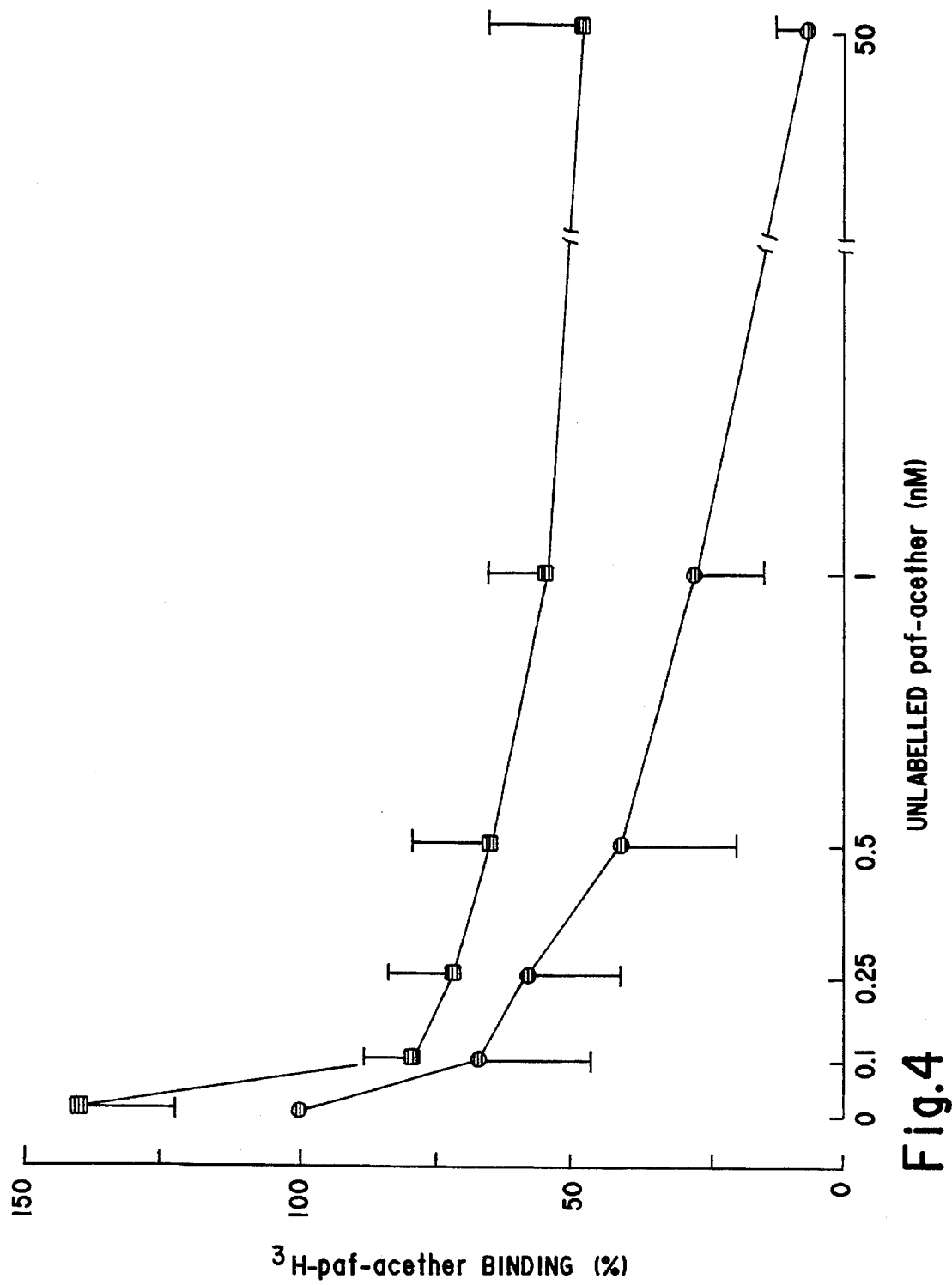
FIG. 4 shows the effect of LDL on $^3$H-paf binding to intact human platelets.

FIG. 4 shows the effect of LDL and LA-paf on $^3$H-paf binding to washed human platelets. The simultanous incubation of platelets with (■) or without (●) LDL and $^3$H-paf (0.065 nM) enhanced the binding of $^3$H-paf. LDL (20 μg per ml) increased total (assessed with paf vehicle, 100%) and non-specific binding assessed with unlabelled paf (50 nM). The values of FIG. 4 correspond to values of table 1 below obtained with the specific paf antagonist WEB 2086.

Figure 5:
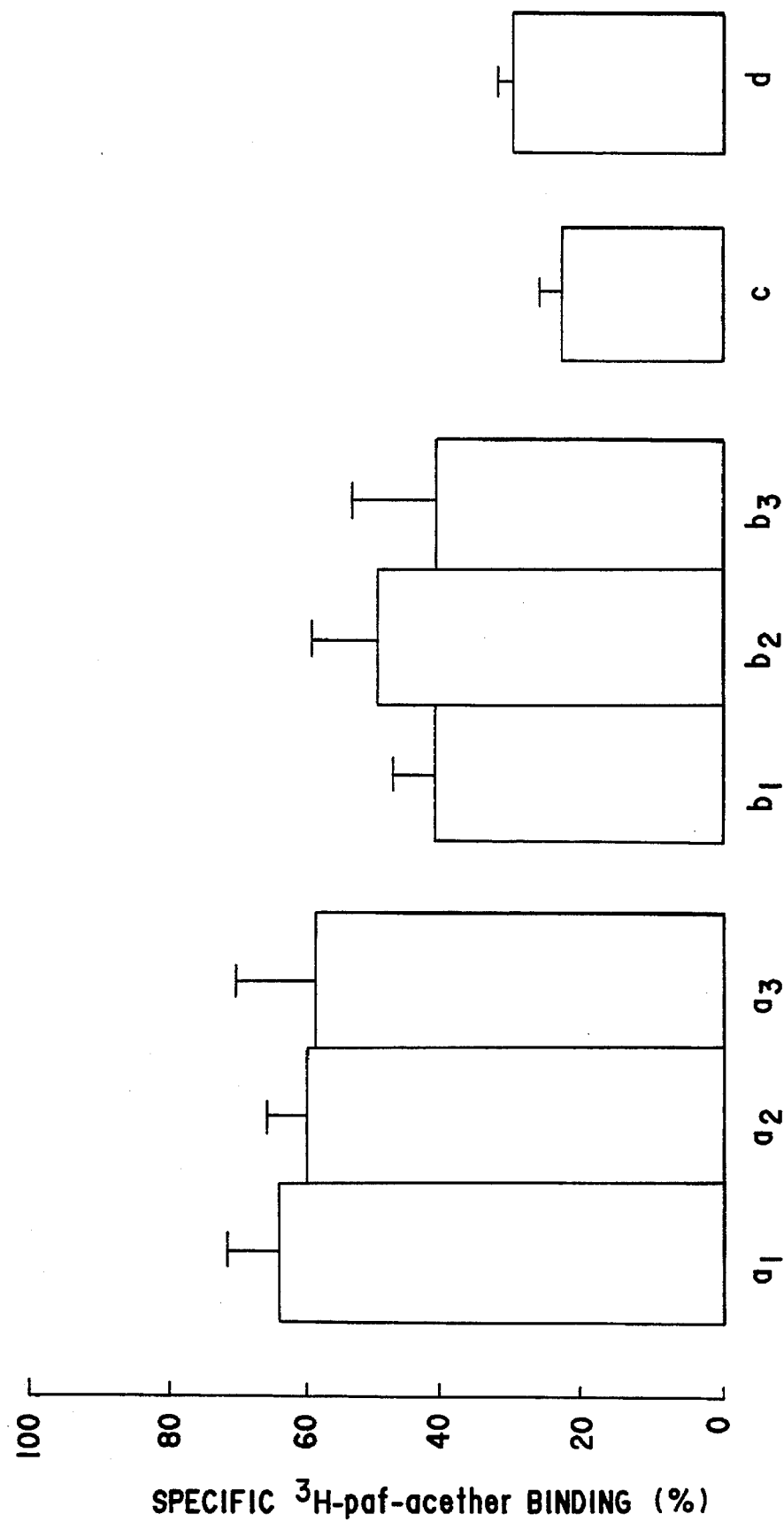
FIG. 5 shows the desensitization of specific $^3$H-paf binding to intact human platelets in response to LA-paf and lipoproteins with effects partly prevented by antibodies against human lipoproteins.

FIG. 5 shows the desensitization of specific paf binding to washed human platelets. If both LDL and LA-paf led to an increase of $^3$H-paf binding to its receptors, a pre-incubation of platelets with both substances in comparison with synthetic paf should decrease the specific $^3$H-paf binding assessed with excess unlabelled paf. Indeed LA-paf (FIG. $5b_{1-3}$) desensitized platelets against a second challenge of paf is compared with vehicle (FIG. $5a_{1-3}$). A similar effect was observed after 3 min. pre-incubation with LA-paf (FIG. $5b_{1-3}$), synthetic paf (FIG. $5c$) or LDL (85 μg per 500 μl, FIG. $5d$). Similarly the LA-paf-mediated (FIG. $5b_2$), but not the synthetically paf-mediated (FIG. $5a_2$) effects were partly prevented when platelets were pretreated with antibodies against human lipoproteins (FIG. $5a_2, b_2$, 2,5 mg per $10^9$ platelets for 40 min. at 20° C.). Pretreatment with polyclonal antibodies against human serum albumin (FIG. $5a_3b_3$) did not modify the LA-paf-mediated desensitization against a second challenge with synthetic paf as compared with the antibody vehicles (FIG. $5a_1b_1$). The observation that antibodies against lipoproteins prevented LA-paf induced desensitization or $^3$H-paf binding against a second challenge of synthetic paf suggested that lipoproteins are causatively involved, thus a lipoprotein portion in LA-paf.

Table 1 below shows the binding of labelled paf-acether to intact washed human platelets in the presence of LA-paf, LDL, synthetic paf-acether and vehicle. LA-paf, synthetic paf (1 nM), LDL (30 μg/ml) or vehicle (water containing 0.2% ethanol) were ed to BSA-buffer. The specific binding of $^3$H-paf (0.065 nM) was verified in the absence and presence, respectively, of an excess of WEB 2086 (1μM).

The values are expressed as fmol bound to $10^8$ platelets and are means ±1 s.d. from three different experiments.

TABLE 1

| $^3$H-paf-binding (fmol) | Vehicle | LA-paf (1 nM) | LDL (30 μg/Mml) | paf (1 nM) |
| --- | --- | --- | --- | --- |
| total | 191 +/− 14 | 262 +/− 23 | 247 +/− 29 | 137 +/− 10 |
| non-specific | 122 +/− 17 | 196 +/− 18 | 159 +/− 17 | 99 +/− 12 |

TABLE 1-continued

| $^3$H-paf-binding (fmol) | Vehicle | LA-paf (1 nM) | LDL (30 μg/Mml) | paf (1 nM) |
|---|---|---|---|---|
| specific | 69 +/− 11 | 81 +/− 32 | 78 +/− 11 | 36 +/− 14 |

As can be seen from table 1, unlabelled paf-acether lowers the total binding of labelled $^3$H-paf to platelets(137±10 fmol)compared pared with vehicle (191±14 fmol) as expected. On the other hand, LA-paf and LDL with 262±23 and 247±29 fmol, respectively, increased the total binding of $^3$H-pal to platelets. The same is true for the non-specific binding and for the specific binding.

Accordingly, there are at least two binding sites on platelets for LA-paf, one binding site being only. accessible for lipoproteins (normal or modified) and LA-paf, respectively, not however for paf-acether.

Table 2 shows the catabolism of $^3$H-paf in the presence of lipoproteins and its metabolism to $^3$H-LA-paf in the presence of lipoproteins and platelets. Platelets did not degrade added $^3$H-paf; but when LDL was present, $^3$H-paf was partly degraded to $^3$H-lyso-paf. A similar degradation was obtained in the presence of VLDL higher concentrations (0.04 % vs 0.17%, w/v, final concentration) as compared to the presence of HDL. The specific paf receptor antagonist WEB 2086 (40 nM) did not interfere with lipoprotein degradation of $^3$H-paf (table 2).

$^3$H-paf was added with or without WEB 2086 (40 nM) to washed human platelets in BSA-buffer containing LDL, HDL or VLDL (0.04%, 0,03% or 0.17%, v/v, final concentrations). Phospholipid analysis was performed with HPLC as described above. Radioactivity of different HPLC retention times was calculated as percentage of the total label after subtraction of the background (but not void volume) values. Values are means ±1 s.d. using LDL, VLDL and HDL from three healthy male volunteers (means ±1 s.d.).

| Retention time | LA-paf | paf | lyso paf |
|---|---|---|---|
| min. | 9–11 | 18–21 | 28–31 |
| BSA-buffer | | | |
| without WEB 2086 | 1.0 ± 1.0 | 90.6 ± 8.8 | 1.9 ± 2.6 |
| with WEB 2086 | 0.3 ± 0.5 | 93.7 ± 3.7 | 2.5 ± 2.8 |
| Platelets | | | |
| without WEB 2086 | 1.9 ± 1.7 | 91.2 ± 2.6 | 1.4 ± 1.6 |
| with WEB 2086 | 0.7 ± 0.6 | 88.5 ± 11.2 | 2.0 ± 2.0 |
| LDL (0.04%) | | | |
| without WEB 2086 | 5.0 ± 1.7 | 47.1 ± 11 | 39.2 ± 4.9 |
| with WEB 2086 | 3.9 ± 1.3 | 41.5 ± 5.7 | 47.3 ± 5.9 |
| HDL (0.03%) | | | |
| without WEB 2086 | 2.9 ± 2.6 | 89.8 ± 3.7 | 4.4 ± 2.9 |
| with WEB 2086 | 1.6 ± 3.2 | 81.0 ± 2.1 | 3.5 ± 1.0 |
| VLDL (0.17%) | | | |
| without WEB 2086 | 0.9 ± 0.5 | 47.6 ± 7.8 | 44.2 ± 0.8 |
| with WEB 2086 | 3.4 ± 5.2 | 44.9 ± 18.6 | 35.8 ± 5.9 |

An amount of labelled LA-paf 5.0±1,7%) was formed when $^3$H-paf was added to the platelet suspension in a LDL and BSA containing buffer (30 min., 20° C.) indicating again its cellular origin.

The specificity of the acetylhydrolase activity was determined by adding LDL (20 μg per 500 μl) to a pH 8.0 EDTA-buffer. In the presence of LDL 54% $^3$h-acetate was released from $^3$H-acetyl-paf (5μM, 10 min at 37° C.) as compared with vehicles or denaturated LDL (100° C. 10 min.). The presence of LA-paf did not lead to formation of $^3$H-acetate from $^3$H-acetyl paf. This excludes the possibility of non-specific binding of labelled lyso paf to platelets in the presence of LA-paf (data not shown).

5. Cultivation and stimulation of monocyte-macrophage-like cells

Monocyte-macrophage-like U 937 cells were grown in a stationary suspension culture in RPMI 1640 medium containing 10% FCS and 2 mM L-glutamine at 37° C. in a humidified atmosphere of 5% $CO_2$ and 95% air. The U 937 cells were diluted (⅒, v/v) twice a week. After three days in culture, the U 937 cells were incubated either in a medium containing 10% delipidated FCS (CPR 1) and 2 mM L-glutamine with either three different LDL preparations (10 μg/ml), cholesterol (10–60 μm/ml), LDL-buffer or ethanol (0.5%, v/v, final concentration) for 2 and 4 and 24 hours.

6. Paf binding studies with monocyte-macrophage-like cells

The U 937 cells were washed twice after sedimentation using centrifugation (100 g×10 min.). After the last wash, the cells were suspended in Tyrode's buffer without $Ca^{2+}$ containing 0.25% BSA. All binding assays were performed in the presence of 1.3 mM $Ca^{2+}$ 1,0 mM $MgCl_2$ and BSA at pH 7.4. $^3$H-paf (50 μl) at different concentrations (0.35–5.6 nM) were added to 400 μl buffer in the absence and presence of an excess of WEB 2086 (1 μm). The reaction was started with 50 μl of cells in suspensions (1.25×10$^6$ final concentration) The U 937 cells were separated from the supernatants by vacuum filtration after 1 h incubation at 4° C.

Figure 6:
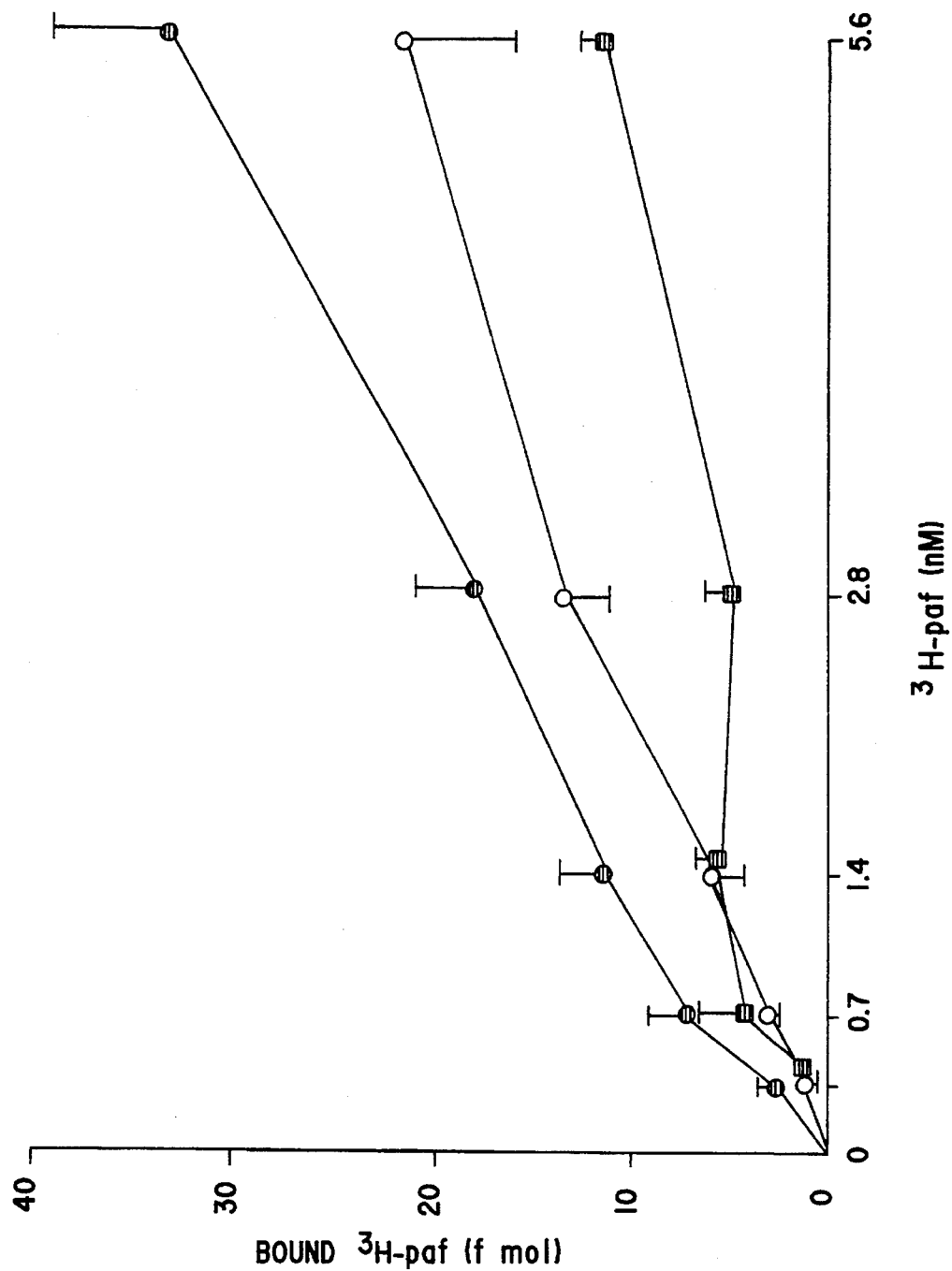
FIG. 6 shows the dose response curve of $^3$H-paf binding to monocyte-macrophage like U 937 cells after incubation in the presence of LDL. The specific $^3$H-paf binding reached saturation in the presence of the triazolothieno-diazepine WEB 2086.

FIG. 6 shows the dose response curve of $^3$H-paf binding after addition of LDL. Three different LDL preparations (10 μg/ml, 24 h) were added to U 937 cells in delipidated medium before three washes. The $^3$H-paf binding to U 937 cells (fmol per 1.2×10$^6$ cells) was measured with (o) and without (●) WEB 2086 (1μM). The cells were separated by vacuum filtration after 1 h incubation at 4° C. The specific binding (■) was calculated from the differences between total and non-specific binding verified in the presence of WEB 2086 (1μM). The values are means ±1 s.d. from three different experiments.

Figure 7:
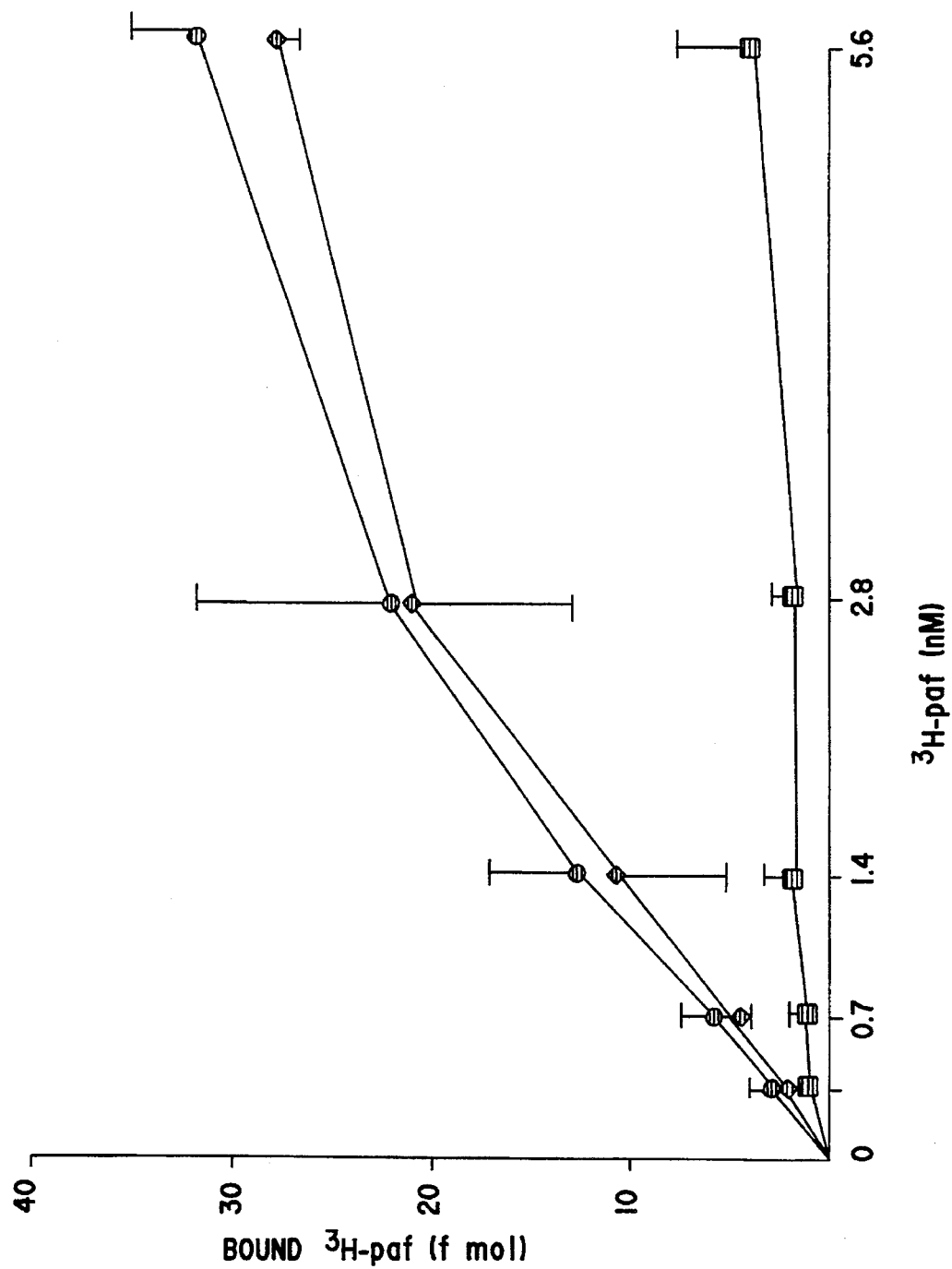
FIG. 7 shows the control dose response curve of $^3$H-paf binding to monocyte-macrophage like U 937 cells kept in 24 hours in delipidated medium with LDL buffer before three washes.

FIG. 7 shows the dose response curve for $^3$H-paf binding to U 937 cells kept 24 h in delipidated medium with LDL-buffer before three washes. The $^3$H-paf binding to U 937 cells (fmol per 1.25×10$^6$ cells) was measured with (♦) and without (●) WEB 2086. The cells were separated by vacuum filtration after an incubation period of 1 h. The specific binding (■) was calculated from the difference between total and non-specific binding verified in the presence of WEB 2086 (1μM). The values are means ±1 s.d. from three different experiments.

Figure 8:
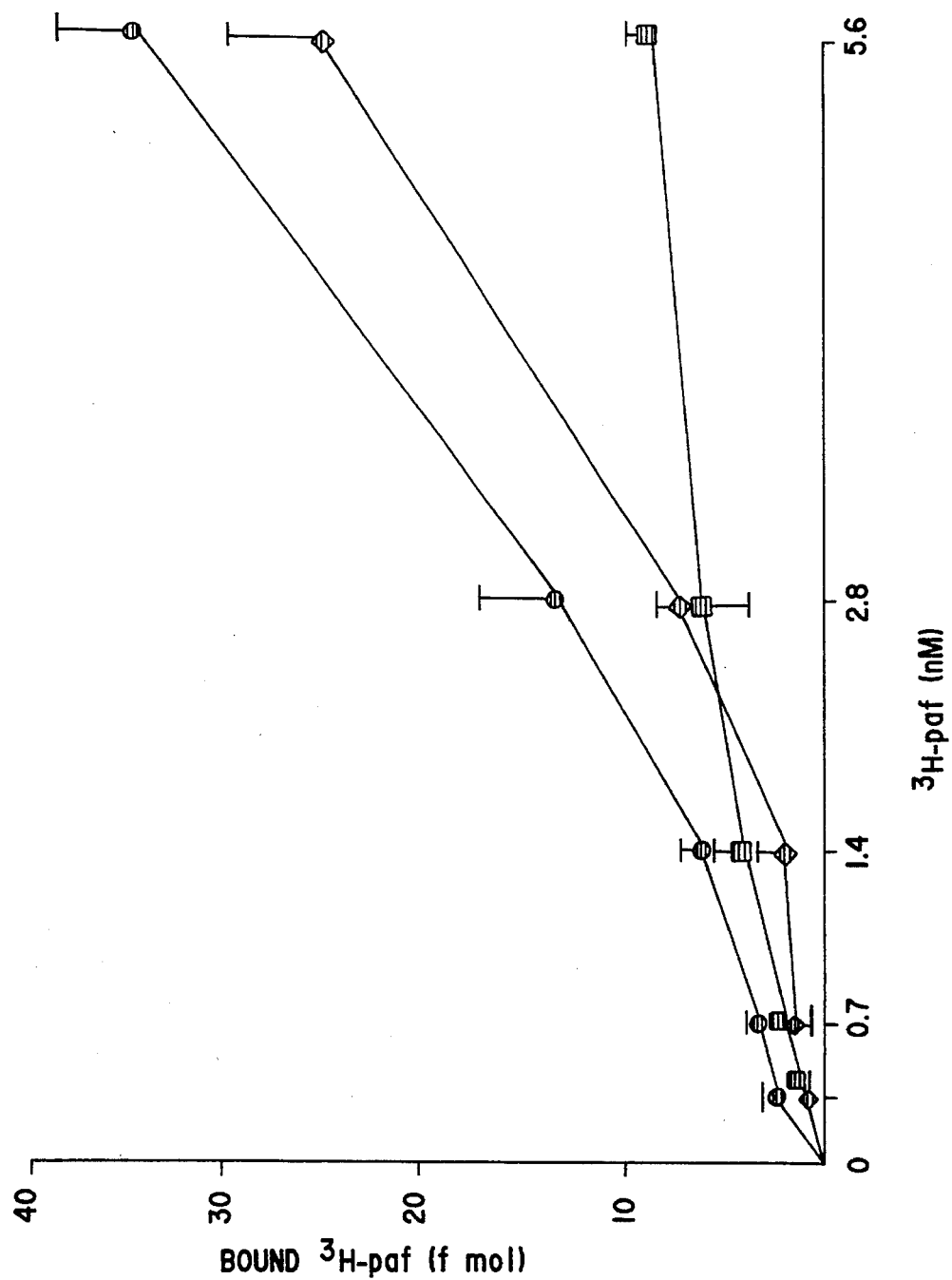
FIG. 8 shows the dose response curve of $^3$H-paf binding to monocyte-macrophage like U 937 cells after incubation in the presence of cholesterol. The specific $^3$H-binding reached saturation in the presence of the triazolothieno-diazepine WEB 2086.

FIG. 8 shows the dose response curve for $^3$H-paf binding after addition of cholesterol. Cholesterol (60 μg/ml, 24 h) was added to U 937 cells kept in delipidated medium before three washes. $^3$H-paf binding to U 937 cells (fmol per 1.25×10$^6$ cells) was performed with (♦) and without (●) WEB 2086. The cells were separated after a 1 h incubation period at 4° C. by vacuum filtration. The specific binding (■) was calculated from the difference between the total and non-specific binding verified in the presence of WEB 2086 (1μM). The values are means ±1 s.d. from three different experiments.

Figure 9A:
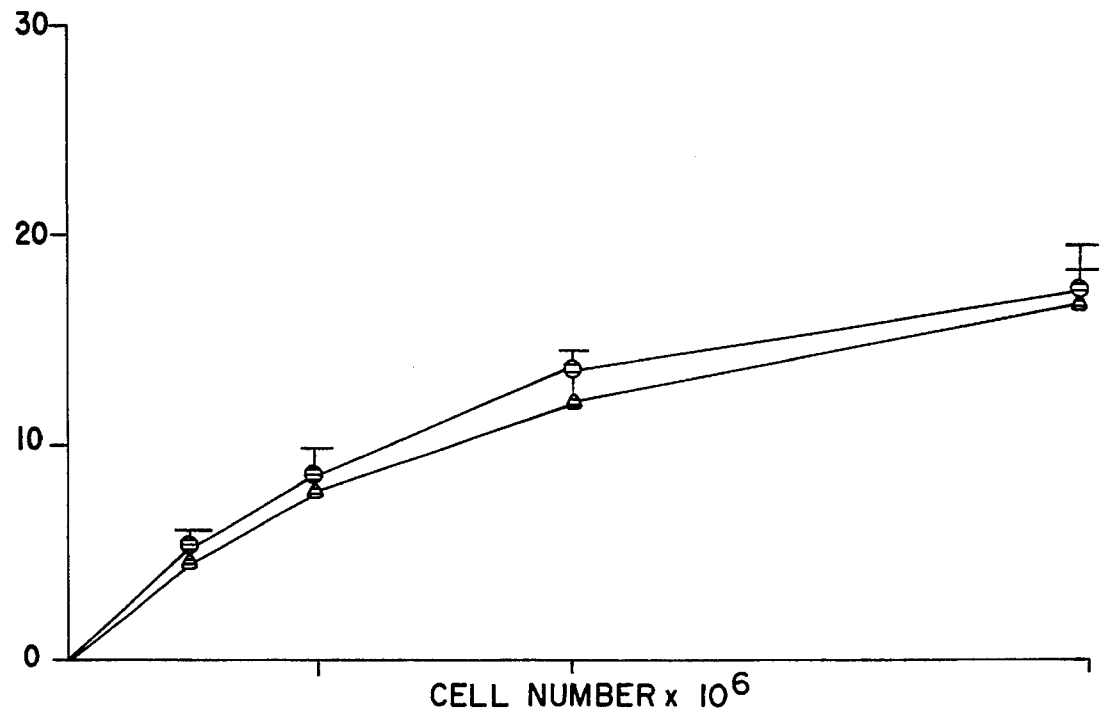
FIG. 9 shows in percent the $^3$H-acetate release from $^3$H-acetyl paf added to an increasing number of U 937 cells. The triazolothieno-diazepine WEB 2086 did not interfere with the metabolism of $^3$H-acetyl paf.
Figure 9B:
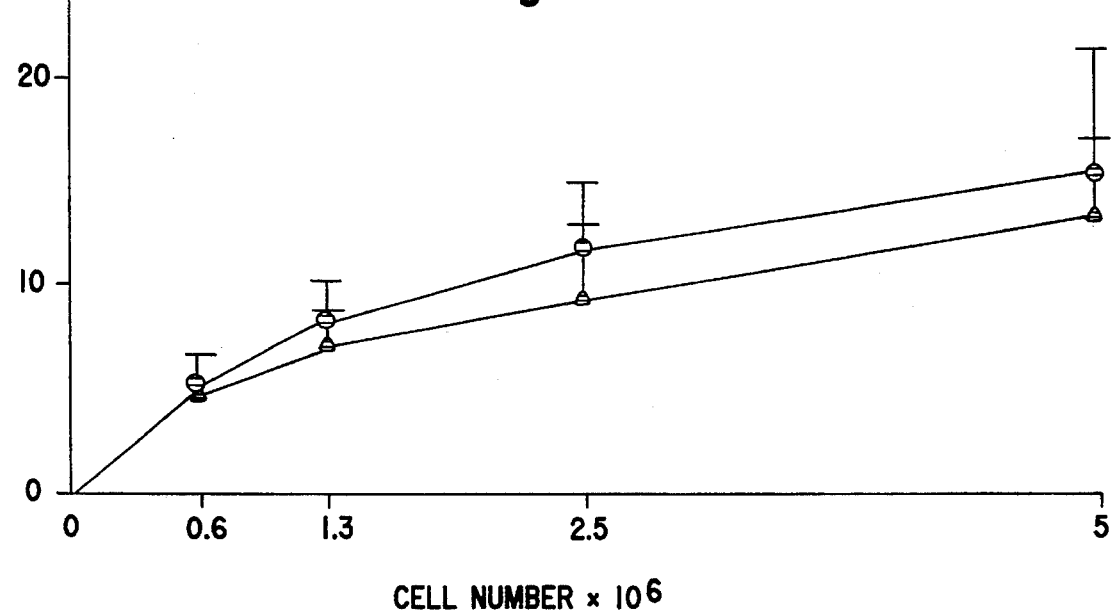

FIG. 9 shows in percent the $^3$H-acetate release from $^3$H-acetyl paf added to increasing numbers of U 937 cells. The U 937 cells were incubated in delipidated medium in the absence (A) or presence (B) of three different LDL preparations (10 μg/ml, 24 h). After 3 washes an increasing number of intact cells was incubated with $^3$H-acetyl-paf (5μM) with (♦) and without (●)

WEB 2086 (1μM) for 15 min. at 37° C. before the reaction was stopped by position in an ice bath. Proteins were denatured by addition of TCA (14 %, v/v.) after a 10 min. incubation with excess BSA and centrifuged. The released $^3$H-acetate was measured in the supernatants. The data are expressed in percent of total added $^3$H-acetyl paf and are means ±1 s.d. of three different experiments.

Specific binding of $^3$H-paf-acether after incubation with LDL:

The monocyte-macrophage-like U 937 cells (1.25×10$^6$) bound $^3$H-paf--acether in a concentration-dependent manner after 1 h incubation at 4° C. without reaching a plateau (FIG. 6 and 7). Addition of three different LDL preparations (10 μg/ml, 24 h) to U 937 cells in delipidated medium before three washes expressed the specific $^3$H-paf binding (FIG. 6) as compared with the non-specific binding with the LDL carrier (FIG. 7).

The total binding of $^{33}$H-paf-acether was similar in LDL-treated U 937 cells vs. control U 937 cells (33.3±5.7 vs. 31.9±3.3 fmol per 1.25×10$^6$ U 937 cells). The non-specific binding verified in the presence of WEB 2086 (1μM) decreased in LDL-treated cells. Thus, the specific binding increased in a significant manner from 1.8±0.8 to 4.6±2.1 fmol (p<0.01 in a "Mann Whitney" test, n=3) at 2.8 nM added $^3$H-paf-acether in LDL-treated cells.

The specific $^3$H-paf-acether binding defined as total binding minus non-specific binding reached plateau values between 1.4 and 2.8 nM added $^3$H-paf-acether. LDL added for shorter incubation periods (2h, 4h) did not express specific binding sites for paf-acether verified again with WEB 2086 (see table 3 below). Neither LDL-treated cells nor control cells catabolised added $^3$H-acetyl paf (5μM, 1 h) under binding conditions at 4° C. (not shown).

Specific $^3$H-paf-acether binding after incubation with cholesterol:

The addition of cholesterol (60 μg/ml, 24h) in delipidated medium to U 937 cells expressed specific $^3$H-paf-acether binding sites in a similar manner as LDL did (FIG. 8). The total binding of $^3$H-paf (5.6 nM) to cholesterol-treated U 937 cells reached similar values as those obtained with LDL-treated cells and control cells (34.4±4.2 fmol vs. 31.9±3.3 3.3 and 33.3±5.7 fmol bound to U 937 cells). The non-specific binding verified with WEB 2086 (1μM) decreased from 34.4±4,2 fmol to 25.2±5.0 fmol in control vs. cholesterol-treated cells, respectively. The specific binding of $^3$H-paf-acether (5.6 nM) resembled that to LDL-treated U 937 cells (9.3±3.6 fmol vs. 11.5±0.7 fmol) as compared with no specific binding to control cells. The specific $^3$H-paf-acether binding reached a similar plateau value with cholesterol and LDL -treated cells (6.2±2.9 fmol vs. 5.7±1.1 fmol) at $^3$H-paf-acether concentrations higher than 2.8 nM. Cholesterol increased the specific binding of $^3$H-paf-acether (0.7 nM) in a concentration-dependent manner by decrease of the non-specific binding (see table 4 below). Again no specific binding was detected when cholesterol was added 2 and 4 h to the delipidated medium (table 3) or after addition of vehicle to the delipidated medium (table 4).

Acetylhydrolase activity of intact U 937 cells:

Intact U 937 cells catabolised added $^3$H-acetyl paf (5μM) at 20° C. in dependence of the cell number (FIG. 9A, B) as compared with no degradation of $^3$H-acetyl paf in the presence of denaturated proteins or in the absence of cells. Addition of three different LDL preparations to U 937 cells in delipidated medium (B: 10 μg/ml, 24 h) did not interfere with paf-acether catabolism of intact U 937 cells as compared with control cells (12.0±1 vs. 13.5±1%) (FIG. 9A, B). Furthermore, the paf-acether receptor antagonist WEB 2086 did not inhibit the catabolism of $^3$H-acetyl-paf on the surface of intact U 937 cells.

Intracellular acetylhydrolase activity after LDL-incubation:

The acetylhydrolase activity was also measured in lysates from washed U 937 cells after LDL-treatment as compared with control cells. The cell lsysates (50 μl) were added to 440 μl of isotonic Hepes/EDTA buffer (pH 8.0), and the reaction was started with $^3$H-acetyl-paf after a pre-incubation of 5 min. at 37° C. After an incubation of 10 min. at 37° C. the reaction was stopped with excess BSA in an ice bath, and after a further incubation of 10 min. the proteins were denatured with TCA (9%, v/v, 0° C. final concentration) The released $^3$H-acetate was measured in the supernatant after centrifugation. The data are expressed in nmol per mg protein.

The acetylhydrolase activity was linear with the protein concentration up to 110 μg/ml through at least 10 min. The enzyme kinetics of control cells kept 24 h in delipidated medium with vehicle were different from LDL-treated cells. The $K_m$ and $v_{max}$ values calculated from the Lineweaver-Burk-plots (see table 5 below) increased after addition of three different LDL preparations to the delipidated medium (10 μm/ml, 24 h). The increase of $v_{max}$ per mg cell protein suggests an enrichment of acetylhydrolase in U 937 cells during incubation in the presence of LDL. The $K_m$ values after incubation with LDL resembled those demonstrated in the plasma.

Table 3 below shows the lack of specific $^3$H-paf-acether binding 2 and 4 h after addition of LDL preparations from three different healthy male volunteers (10 μg/ml) or cholesterol (60 μg/ml) to U 937 cells in delipidated medium as compared with vehicle. The cells were washed three times and $^3$H-paf-acether binding (1.6 nM) was performed with and without WEB 2086 (1μM, 1 h, 4° C., 0.25% BSA) before cells were separated by vacuum filtration. Specific binding is defined as total binding minus non-specific binding verified with WEB 2086. Values are expressed in fmol per 1.25×10$^6$ U 937 cells and are means ±1 s.d. of three different experiments.

TABLE 3

| Cell incubation | 2 h | 4 h |
| --- | --- | --- |
| Vehicle | 6.1 +/− 1.2 | 4.7 +/− 0.6 |
| LDL without WEB 2086 | 4.7 +/− 0.6 | 4.1 +/− 1.7 |
| LDL with WEB 2086 | 4.0 +/− 1.0 | 4.0 +/− 1.3 |
| Cholesterol without WEB 2086 | 3.7 +/− 1.4 | 5.0 +/− 2.2 |
| Cholesterol with WEB 2086 | 3.6 +/− 1.0 | 5.7 +/− 1.5 |

Table 4 below shows the cholesterol dose dependence of the specific $^3$H-paf binding to U 937 cells (24 h). Cholesterol was added to U 937 cells in delipidated medium as compared with vehicle (0.5% ethanol, v/v) and cells were washed three times after a 24 h incubation period. $^3$H-paf-acether binding (0,7 n M) was performed with and without WEB 2086 (1μM, 1 h, 4° C., 0.25 % BSA ) before cells were separated by vacuum filtration. Specific binding is defined as total binding minus non-specific binding verified with WEB 2086 and values are expressed as fmol per $1.25 \times 10^6$ U 937 cells. They are means ±1 s.d. of three different experiments.

TABLE 4

| Cell incubation Cholesterol | total binding | non-specific binding | specific binding |
|---|---|---|---|
| Vehicle | 4.1 +/− 1.0 | 3.4 +/− 0.5 | 0.6 +/− 0.4 |
| 10 µg/ml | 4.1 +/− 1.2 | 3.2 +/− 1.0 | 1.0 +/− 0.9 |
| 60 µg/ml | 3.0 +/− 0.3 | 1.3 +/− 1.2 | 1.7 +/− 0.9 |

Table 5 below shows the acetylhydrolase enzyme kinetics of lysed U 937 cells 24 h after addition of LDL preparations from three healthy male volunteers (10 µm/ml) to delipidated medium as compared with vehicle. U 937 cells were lysed by sonication (3 times for 30 sec.) after three washes and the release of $^3$H-acetate from $^3$H-acetyl paf during 10 min. incubation at 37° C. was verified. The reaction was stopped with excess BSA and protein denaturation (TCA, 9%, v/v, 0° C.). The $K_m$ and $v_{max}$ values are from a Lineweaver-Burk-plot from three different experiments and are means ±1 s.d. from three different experiments.

TABLE 5

| Incubation | proteins (µg/ml) | $K_m$ (µM) | $v_{max}$ (nmol/min/mg) |
|---|---|---|---|
| Vehicle | 104.0 +/− 10.0 | 2.0 +/− 0.5 | 0.2 +/− 0.04 |
| LDL | 102.0 +/− 8.0 | 9.4 +/− 1.9 | 0.5 +/− 0.2 |
| (10 µg/ml) | n.s. | $p < 0.02$ | $p < 0.02$ |

I claim:

1. A method for treating hyperlipidemia in a patient, comprising the step of administering to the patient an effective amount of a triazolothieno diazepine wherein the triazolothieno diazepine is selected from the group consisting of 3-(4-(2-chlorophenyl)-9-methyl-6H-thieno (3,2-f) (1,2,4) triazolo-(4,3-a)(1,4) diazepine-2yl-1-(4-morpholinyl)-1-propanone (WEB 2086); 3-(4-(2-chlorophenyl)-9-cyclopropyl-6H-thieno (3,2-f) (1,2,4) triazolo-(4,3-a) (1,4) diazepine-2yl-1-(4-morpholinyl)-1-propanone (WEB 2098); or tetrahydro-4,7,8,10 methyl-(chloro-2phenyl) 6[dimethoxy-3,4-phenylthio]methylthiocarbonyl-9pyrido [4',3'-4,5]thieno[3,2-f]triazolo-1,2,4[4,3-a]diazepine-1,4 (BN 50739).

* * * * *

UNITED STATES PATENT AND TRADEMARK OFFICE
CERTIFICATE OF CORRECTION

PATENT NO. : 5,480,881

DATED : January 2, 1996

INVENTOR(S) : KORTH

It is certified that error appears in the above-identified patent and that said Letters Patent is hereby corrected as shown below:

In the Drawing:

[Figure 9], sheet 9, the vertical axis should be labeled --$^3$H acetate release(%)--.

Column [1], line 34, please delete "i s", insert therefor --is--. Line 47, please delete "6[dimethoxy 3,4-phenyl", insert therefor --6[(dimethoxy-3, 4-phenyl--. Line 62, please delete "[2-d]", insert therefor --[1 ,2-d]--.

Column [4], line 17, please delete "cyte-macro-phage-like", insert therefor --cyte-macrophage-like--.

Column [5], line 25, please delete "does", insert therefor --dose--.

Column [6], line 2, please delete "955", insert therefor --1955--. Line 13, please delete "5", insert therefor --15--. Line 15 please delete "(100μM)for", insert therefor --(100μM) for--. Line 35 please delete "cells cultured in standard", insert therefor --cells (cultured in standard--. Line 37 please delete "(½, v/v)", insert therefor --(1/2, v/v)--.

UNITED STATES PATENT AND TRADEMARK OFFICE
CERTIFICATE OF CORRECTION

PATENT NO. : 5,480,881

DATED : January 2, 1996

INVENTOR(S) : KORTH

It is certified that error appears in the above-identified patent and that said Letters Patent is hereby corrected as shown below:

Column [6], line 42, please delete "Microporsil" insert therefor --Microporasil--. Line 50, please delete "asparinated" insert therefor --aspirinated--.

Column [7], line 2, please delete "paf" insert therefor --Paf--. Line 43, please delete "pal" insert therefor --paf--.

Column [8], line 55, please delete "were ed" insert therefor --were added--.

Column [9], line 11, please delete "fmol)compared" insert therefor --fmol) compared--. Line 14, please delete "pal" insert therefor --paf--. line 18, please delete "only. accessible" insert therefor --only accessible--.

UNITED STATES PATENT AND TRADEMARK OFFICE
CERTIFICATE OF CORRECTION

PATENT NO. : 5,480,881
DATED : January 2, 1996
INVENTOR(S) : KORTH

It is certified that error appears in the above-identified patent and that said Letters Patent is hereby corrected as shown below:

Column [9], table 2, please substitute the paragraphs as indicated: No new paragraphs on lines 47, 50, 53, 57 and 60. Table 2 please insert new paragraphs on lines 48, 53, 56 and 58. Line 64, please delete "paf 5.0" insert therefor --paf(5.0--.

Column [10], line 11, please delete "$^3$h" insert therefor --$^3$H--. Line 23, please delete "($^1/_{10}$, v/v)" insert therefor --(1/10, v/v)--. Line 27, please delete "(10-60 $\mu$m/ml)" insert therefor --10-60 $\mu$g/ml--. Line 39, please delete "tration)" insert therefor --tration).--.

Column [11], line 12, no new paragraph. Line 23, please delete "$^3$H-paf--/acether" insert therefor --$^3$H-paf-/acether--.

UNITED STATES PATENT AND TRADEMARK OFFICE
CERTIFICATE OF CORRECTION

PATENT NO. : 5,480,881

DATED : January 2, 1996

INVENTOR(S) : KORTH

It is certified that error appears in the above-indentified patent and that said Letters Patent is hereby corrected as shown below:

Column [11], line 54, please delete "3.3", line 56, please delete "34.4±42" insert therefor --34.4±4.2--.

Column [12], line 5, please delete ")at" insert therefor --) at--. Line 35, please delete "µm" insert therefor --µg--.

Column [13], Line 16, please delete "µm" insert therefor --µg--.

UNITED STATES PATENT AND TRADEMARK OFFICE
CERTIFICATE OF CORRECTION

PATENT NO.  : 5,480,881
DATED       : January 2, 1996
INVENTOR(S) : Korth

It is certified that error appears in the above-indentified patent and that said Letters Patent is hereby corrected as shown below:

Column [14], line 19, please delete "tetrahydro-4,7,8,10 methyl-(chloro-2phenyl)" insert therefor --tetrahydro-4,7,8,10 methyl-(chloro-2 phenyl)--. Line 20, please delete "6[dimethoxy-3,4-phenylthio]methylthiocarbonyl-9pyrido" insert therefor --6[(dimethoxy-3,4-phenyl)thio] methylthiocarbonyl-9 pyrido--.

Signed and Sealed this

First Day of April, 1997

Attest:

BRUCE LEHMAN

*Attesting Officer*    Commissioner of Patents and Trademarks